United States Patent [19]

Latos

[11] 4,208,240
[45] Jun. 17, 1980

[54] METHOD AND APPARATUS FOR CONTROLLING PLASMA ETCHING

[75] Inventor: Thomas S. Latos, Carpentersville, Ill.

[73] Assignee: Gould Inc., Rolling Meadows, Ill.

[21] Appl. No.: 6,627

[22] Filed: Jan. 26, 1979

[51] Int. Cl.$^2$ .................... H01L 21/306; H03K 5/18; H03K 5/20
[52] U.S. Cl. .................... 156/627; 156/643; 156/345; 328/132; 356/381; 356/448
[58] Field of Search .............. 156/345, 626, 627, 643; 356/381, 445, 448; 328/114, 132, 150

[56] References Cited

U.S. PATENT DOCUMENTS

| | | | |
|---|---|---|---|
| 3,596,190 | 7/1971 | Marshal | 328/132 |
| 3,711,779 | 1/1973 | Allington | 328/114 |
| 3,808,067 | 4/1974 | Brown | 156/627 |
| 4,135,161 | 1/1979 | Torrieri | 328/114 |

FOREIGN PATENT DOCUMENTS 1023826  9/1974  Canada .................... 156/627

OTHER PUBLICATIONS

Price, "Etch and-Paint Detection," IBM Technical Disclosure Bull. vol. 15, No. 11 (4/73), pp. 3532-3533.
Dhaliwal et al, "Multiple Sensor . . . System," IBM Technical Disclosure Bull. vol. 17, No. 17 (12/74), p. 1946-1947.
Moritz, "Continuous . . . Layers," IBM Technical Disclosure Bull. vol. 19, No. 7 (12/76), pp. 2579-2580.

*Primary Examiner*—Jerome W. Massie
*Attorney, Agent, or Firm*—Charles E. Snee, III; Russell E. Baumann

[57] ABSTRACT

A method and apparatus are disclosed for controlling plasma etching processes in which a thin layer is etched away to expose a substrate. Coherent light is directed onto the surface being etched, so that the change in reflectivity of the surface upon exposure of the underlying substrate produces a detectable change in the characteristics of the light reflected. A derivative detector having a variable timer is provided to sample continuously the reflected light and provide a control signal in response to a predetermined change in the characteristics of the light reflected, which is used to terminate the plasma etch process before an overetch condition occurs. The method and apparatus of the invention will detect a desired end point of etching through insulation to an underlying metal substrate, through metal to an underlying insulation substrate, through one insulation type to an underlying substrate of another insulation type and through one metal to an underlying substrate of another metal.

4 Claims, 5 Drawing Figures

METHOD AND APPARATUS FOR CONTROLLING PLASMA ETCHING

CROSS REFERENCE TO RELATED APPLICATION

This application discloses an improvement on the invention disclosed in the application of Heinz H. Busta, Robert E. Lajos and Kul H. Bhasin for A Method and Apparatus for End Point Detection During Plasma Etching filed Dec. 5, 1977 under Ser. No. 857,384. The contents of this earlier application are hereby incorporated by reference into the present application.

BACKGROUND OF THE INVENTION

DESCRIPTION OF THE PRIOR ART

In the manufacture of integrated circuits and similar devices, it is common practice to etch through a first thin layer in a prescribed or predetermined pattern to expose an underlying substrate. When the thin layer is of electrically insulating material, the substrate typically will be either a metal or a semi-conductive material. After the prescribed pattern has been etched through the layer of insulation, another layer of metal or semi-conductive material may be applied over the insulation to come into contact with exposed portions of the underlying substrate. During initial and/or subsequent etching processes, after the outermost layer of material is etched away, an overetching condition begins to take place, the magnitude of which is a function of the plasma etching parameters. If the etching process is not terminated soon after overetching begins, a defective unit may result.

Typically, light reflected from an insulation material undergoing etching will produce a low frequency signal in the order of about 0.005 Hz from an optical detector. This low frequency or undulating signal is produced by constructive and destructive interference of the reflected light waves. When an insulation layer is completely etched away to expose a metal layer, the detector will produce an essentially constant or DC signal to indicate the presence of metal. Prior art systems are known which can detect the transition from insulation to metal but not the transition from metal to insulation. Also, prior art systems of the type incorporating digital signal analysis techniques employ analog to digital converters whose conversion times have no relationship to the process being controlled. Such systems typically require both analog and digital filtering circuitry because of the low frequency signal obtained from the detector.

Various techniques have been developed in the past for monitoring the progress of an etching process to determine when a surface layer has been etched away to reveal an underlying substrate. An etch end-point detector was disclosed by R. N. Price in IBM Technical Disclosure Bulletin Vol. 15, No. 11, pp 3532-33, dated April, 1973, in which light reflected from a surface undergoing etching is monitored to detect changes in the light characteristics indicative of the desired end point. An output signal is generated when the derivative of the light signal with respect to time is zero for a period of time. Thus, etching through an insulation layer to an underlying metal layer may be monitored. Another such end-point detection system was disclosed by J. C. Collins and P. J. Pavone in IBM Technical Disclosure Bulletin Vol. 17, No. 5, pp 1342-43, dated October, 1974; however, this system is not readily adaptable to detect transitions from low derivative to high derivative of the light signal. A related technique also was disclosed by H. Moritz in IBM Technical Disclosure Bulletin Vol. 19, No. 7, pp 2579-80, dated December, 1976, in which the intensity of reflected light is recorded and observed to detect end-point. Finally, R. C. Lewis in U.S. Pat. No. 4,041,404, Apparatus and Method for Detecting When a Measured Variable Represented By a String of Digital Pulses Reaches a Plateau, issued Aug. 9, 1977, disclosed a system for monitoring changes in the derivative of a time-varying signal.

While these prior art end-point detection systems each have certain advantages, none of them provides a closed loop control function which will terminate the etching process when the desired end-point has been reached. Moreover, they appear to be rather sensitive to circuit noise from typical electrical noise sources and also provide no flexibility in analog-to-digital conversion times which would permit the system to track various etching processes having differing characteristics. Finally, their capability to detect the end-point of metal-to-insulation or insulation-to-insulation etching is rather doubtful.

OBJECTS OF THE INVENTION

An object of the present invention is to provide a closed-loop end-point detection system for use in wet or plasma etching systems.

Another object of the invention is to provide such a detection system which is relatively insensitive to typical electrical noise.

A further object of the invention is to provide such a system which is useful with a wide variety of etching processes which proceed at differing rates.

Yet another object of the invention is to provide such a system which will detect the end-point of metal-to-metal, insulation-to-insulation, metal-to-insulation and insulation-to-metal etching processes and control the processes accordingly.

These objects are only exemplary; thus, other desirable objectives inherently achieved by the disclosed process and apparatus may occur to those skilled in the art. Nonetheless, the scope of the invention is to be limited only by the appended claims.

SUMMARY OF THE INVENTION

The above objects and other desirable advantages are achieved by the method and apparatus of the invention in which a layer undergoing etching is caused to reflect a beam of radiation and the reflected radiation is monitored by a suitable detector to produce a signal. The time derivative of the signal is determined for successive intervals and compared to predetermined criteria indicative of end point. When the criteria are satisfied, the etching process is terminated automatically. End points reached while etching a variety of material pairs, may be detected.

DETAILED DESCRIPTION OF THE INVENTION

Figure 1:
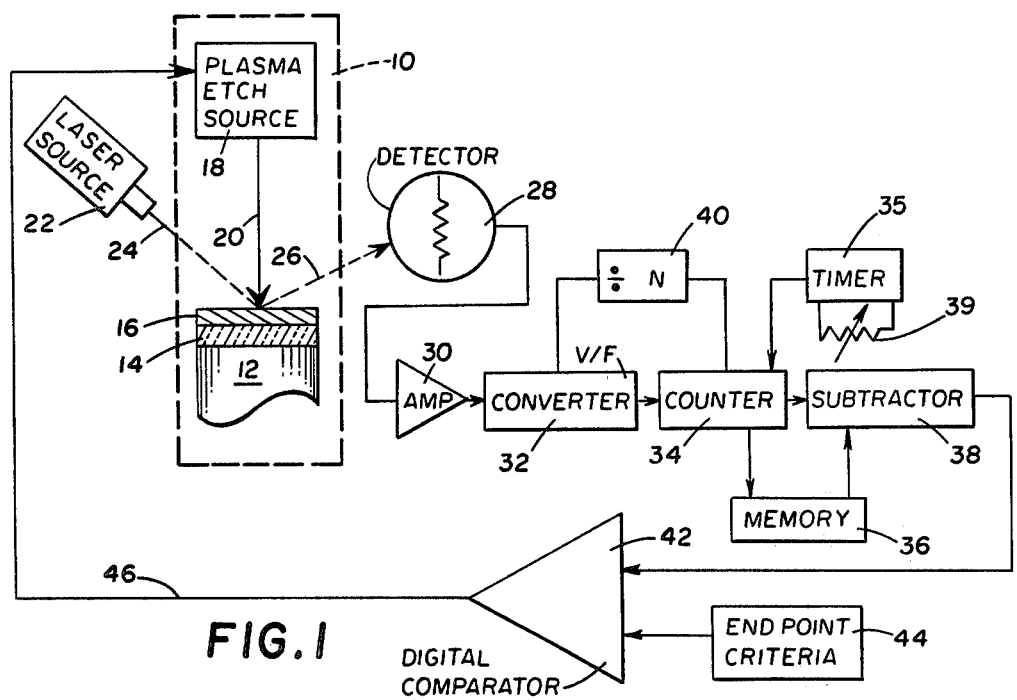
FIG. 1 is a block diagram illustrating apparatus used to carry out the method of this invention.

The apparatus of the present invention is illustrated in FIG. 1. A plasma etching chamber 10 is provided in which a unit 12 forms a support body for one or more layers of insulation or metal or both, in any combination or sequence. For example, unit 12 may comprise a first, underlying layer 14 of insulation and a second, overlying layer 16 of metal.

Layers 14 and 16 are plasma etched, in predetermined patterns using a conventional plasma etch source 18 and photolithographic techniques. The invention may also be used with wet etching systems. A plasma etch source 18 directs a plasma beam 20 onto the surface of the layer to be etched so that eventually the underlying substrate is exposed. Preferably, the plasma beam composition is tailored to etch only the outermost layer; however, this is not possible for all material combinations.

A laser source 22 or other coherent light source directs a light beam 24 on the surface of the layer being etched. Reflected light beam 26 impinges upon a photodetector 28 to produce an electrical output signal. For example, when the plasma beam 20 is etching through metal, the electrical signal produced by detector 28 will be essentially a DC signal. On the other hand, when the plasma beam 20 is etching through insulation, the electrical signal produced by detector 28 will be a very low frequency or undulating signal proportional to the etch rate. For example, the signal frequency is about 0.005 Hz when etching tantalum oxide at a rate of approximately 1000 Angstroms per minute. The signal sensed by detector 28 is amplified by an amplifier 30 coupled to a voltage-to-frequency converter 32. The frequency of the output of converter 32 will be a function of the magnitude of the voltage applied to the converter. The output pulses are fed to a counter 34 which is enabled by an adjustable timer 35. The counting or enable period of timer 35 preferably is chosen in the range of 1 to 5 seconds so as to optimize noise rejection of typical electrical noise sources and still maintain good transient response when detecting the end point. If the output voltage of amplifier 30 changes during the next counting period or time frame, so also does the frequency of the output pulses from converter 32.

The output of the counter 34 during an initial counting period is applied to a memory circuit 36; and the output during the next counting perod, to a subtractor circuit 38. The initial count stored in memory circuit 36 is applied to subtractor circuit 38 simultaneously with the next count from counter 34. The next or present count of pulses is subtracted from the initial or previous count, so that the difference is proportional to the derivative or slope of the signal sensed by detector 28. It will be understood that the operation of subtractor circuit 38 may be reversed and the initial or previous count subtracted from the next or present count to provide equally useful derivative information. Sequencing of counter 34, memory 36 and subtractor 38 is achieved by timer 35 in a manner well known in the art. In accordance with this invention, timer 35 is provided with adjusting means 39 so that the enable or counting period of the counter 34 can be selected in accordance with the process being used. To extend the range of operation of the present invention, a divide by N circuit 40 is connected between the voltage-to-frequency converter 32 and the counter circuit 34. The divider circuit 40 will allow a higher number of pulses to be generated within the converter 32 without requiring expansion of the counter 34, when using long counter periods for slow etch rates.

The output of subtractor 38 is applied to one input of a digital comparator 42. Another input of the comparator 42 receives signals from an end point criteria generator 44 which may be any suitable programmer of the keyboard type. When the signals from subtractor 38 correspond to the information in generator 44, comparator 42 will produce a control signal on output line 46. This control signal is applied to plasma etch source 18 to terminate it operation before an overetch condition can occur.

Figure 2:
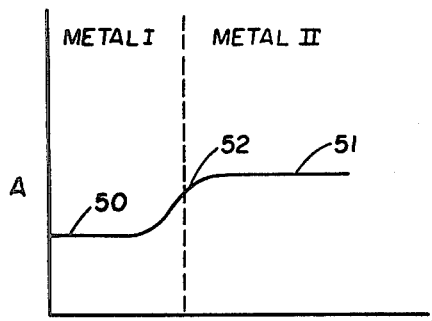
FIG. 2 illustrates detector signal amplitude vs. etch time of etching through one metal to expose another metal.

For a better understanding of the present invention refer now to FIGS. 2, 3, 4 and 5, where various detector signals are shown. FIG. 2 illustrates a time vs. amplitude signal obtained from the detector 28 when etching through one type of metal to expose another type of metal. The portion 50 of the signal trace representing one metal is substantially a straight line as is the portion 51 which represents another metal. The derivative of horizontal straight line portions 50 and 51 each is zero or substantially zero. However, the curved portion 52, connecting the straight portions 50 and 51, has a derivative which is non-zero. The circuitry shown in FIG. 1 detects the transition from zero slope to non-zero slope as an indication of the end point and terminates operation of plasma etch source 18. While FIG. 2 shows a process of etching through one metal to expose another metal in which the signal increases with time, it will be understood that the signal may decrease with time to indicate the transition.

Figure 3:
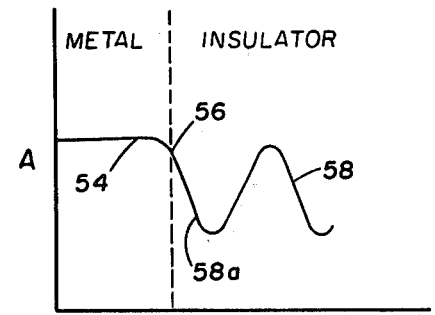
FIG. 3 illustrates detector signal amplitude vs. etch time of etching through metal to expose insulation.

FIG. 3 illustrates a time vs. amplitude signal obtained from detector 28 when etching through metal to expose insulation. The straight line portion 54 represents metal being etched away, and during this etching process the derivative of the detector signal is substantially zero. At point 56 the straight line portion 54 begins to vary at a low frequency, typically about 0.005 Hz, as indicated by reference numeral 58. The initial portion 58a has a substantially non-zero derivative which causes a control signal to appear at the output of comparator 42, thus terminating operation of plasma etch source 18. Therefore, as soon as the system of the present invention senses full exposure of the insulation substrate, etching is stopped and overetching is prevented.

Figure 4:
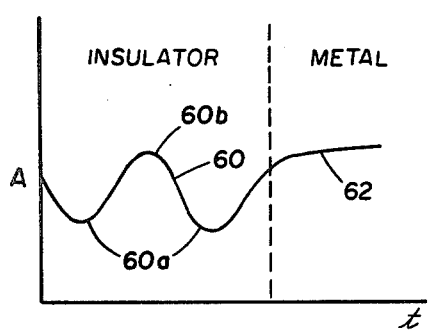
FIG. 4 illustrates detector signal amplitude vs. etch time of etching through insulation to expose metal.

FIG. 4 illustrates a time vs. amplitude signal obtained from the detector 28 when etching through insulation to expose metal. Here a low frequency signal 60, typically about 0.005 Hz, indicates that insulation material is being etched. The derivative of such a signal is always non-zero except at the minima and maxima points 60a and 60b, respectively. However, the time interval of the minima and maxima points is short compared to preselected information set into criteria generator 44. Therefore, no control signal is generated and plasma etching continues. When etching of insulation is completed, and metal is fully exposed, a DC signal 62 is sensed by detector 28. The DC signal 62 produces a zero derivative during a time interval much longer than that during which zero derivative was sensed at minima and maxima points 60a and 60b; so that the requirements of criteria generator 44 are met and a control signal is generated to terminate operation of the etching apparatus, thereby eliminating overetching of the exposed metal substrate.

Figure 5:
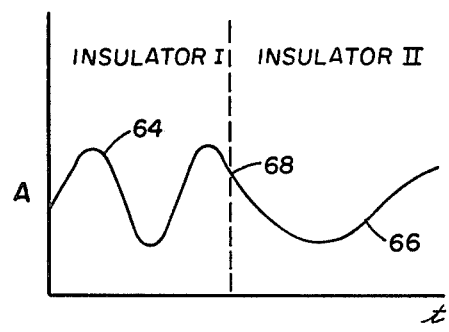
FIG. 5 illustrates detector signal amplitude vs. etch time of etching through one type of insulation to expose another type of insulation.

FIG. 5 illustrates a time vs. amplitude signal obtained from the detector 28 when etching through one type of insulation to expose another type of insulation. The curved portion 64 represents detector response for the insulation initially etched away; and curved portion 66, for the insulation subsequently exposed. Curved portion 64 is here shown as being of a higher frequency than curved portion 66, the difference being caused by the plasma composition which yields different etch rates for different materials. The transition point 68 between the two curved portions 64 and 66 is sensed by detector 28 and the preselected condition, as set into the criteria 44, will cause a control signal to be generated and terminate operation of the etching apparatus, as the portion of the curve 66 has an average derivative whose magnitude is less than that generated while on the portion 64 of the curve.

The criteria generator 44 receives input information regarding the number of consecutive time frame units during which an indication of end-point conditions must be sensed before a control signal is released on line 46. In one embodiment five time frames are required to confirm the existence of the desired condition, each time frame being from one to five seconds, more or less, in length. This long time frame arrangement integrates out contributions due to typical electrical noise sources of less than 10 Hz. In addition, when subtraction is performed by subtractor 38 DC errors such as that obtained by component drift are also eliminated.

The end point information used by criteria generator 44 are inserted manually or by other suitable means and are based on experimental data. The changes in detector output illustrated in FIGS. 2 to 5 follow the general forms shown; however, those skilled in the art will appreciate that signal magnitudes, frequencies and the like will vary depending on the process parameters and the materials involved. For the conditions of FIGS. 2 to 4, a sample of the layers of interest is placed in a plasma etcher and then deliberately etched beyond the end point, as noted on the analog recording of the detector output. Provided actual etching conditions are maintained close to those of such a calibration run, the analog trace will be representative of future etching runs as well. The system of FIG. 1 is set so that a change in count of at least 10 (the threshold) is required to indicate an end point, and such a change must be recorded at least ten times in succession (the pass number). The difference counts recorded during the actual calibration run are compared to the recorded trace. For an insulator-to-metal etch such as in FIG. 4, the low derivative or threshold value indicative of end point is determined by the difference count values following end point; and the number of successful sequential tests required, the pass number, is determined by that number which is necessary to avoid triggering at the minimum or maximum points. The counter enable time is selected based on the maximum acceptable overetch beyond the first layer into the second. For example, if the particular plasma etching process will yield an etch rate of "A" Angstroms per unit time into the second layer and the maximum acceptable overetch is "B" Angstroms, then the maximum allowable increment of time, within which the system according to the invention must be able to determine whether end point has arrived, is "B/A" units of time. If the pass number for the process is "C" consecutive indications of end-point, then the enable time is chosen to be "B/2AC" since each indication of end point requires comparison of two consecutive counts. As mentioned previously, the provision of adjustment means 30 on timer 35 permits selecting the counter enable time as necessary to suit the particular process being controlled and thereby to ensure that a maximum permissable overetch is not exceeded. Similar techniques are used for the cases illustrated in FIGS. 2 and 3. Using such criteria, overetch is estimated at less than 1000 A.

For the case shown in FIG. 5, a somewhat different technique usually is required to determine the end point criteria since the change in detector signal usually is less dramatic. Where the etch rates of the two insulators are quite different, say, by a factor of 10, then the previously described technique is applicable. However, where the etch rates of the two materials are similar, the time between maxima or minima is monitored. The derivative of the detector output will undergo a sign change at these regularly spaced points. However, when the end point has passed, the spacing between maxima or minima will change, signalling end point. That is, prior to end point, a slope sign change will occur during each time increment, provided the increments are chosen to always include a maximum or a minimum. After end point, the apparatus will continue to look for a sign change in each time increment, the absence of the change in a selected number of increments being indicative of end point.

While a single system is illustrated to perform the method of this invention it will be understood variation and modification may be effected without departing from the spirit and scope of the following claims.

The invention claimed is:

1. A method for etching a first layer of material to expose an underlying layer of a second material, comprising the steps of:
    exposing said first layer to an etching medium;
    projecting a beam of coherent radiation onto the surface of said first layer, and in sequence said second layer, during etching;
    detecting radiation reflected from said first or second layer and producing a first analog signal in response thereto;
    determining the time derivative of said analog signal during successive intervals, each interval being of a length in time selectably chosen to ensure a maximum acceptable overetch beyond said first layer into said second layer;
    comparing the derivative determined for each successive interval to predetermined criteria indicative of the end-point of etching between said layers and providing a control signal upon achievement of end-point; and
    terminating said exposing step in response to said control signal.

2. A method according to claim 1, wherein said determining step comprises the steps of:
    converting said analog signal to a train of pulses occuring at a frequency proportional to said analog signal;
    counting said pulses during successive intervals, each interval being of a length in time selectably chosen to ensure a maximum acceptable overetch beyond said first layer into said second layer; and comparing the count of pulses in successive intervals to provide a train of signals proportional to the time derivative of said analog signal.

3. Apparatus for etching a first layer of material to expose an underlying second layer, comprising:
means for exposing said first layer to an etching medium;
means for projecting a beam of coherent radiation onto the surface of said first or second layer during etching;
means for detecting radiation reflected from said first layer or said second layer during etching and for producing a first analog signal in response thereto;
means for converting said signal to a train of pulses occuring at a frequency proportional to said first signal;
means for counting said pulses during successive intervals, each interval being of a length in time selectably chosen to ensure a maximum acceptable overetch beyond said first layer into said second layer;
means for comparing the count of pulses in successive intervals to provide a train of signals porportional to the slope of said analog signal;
means for storing criteria indicative of the end-point of etching between said layers;
means for comparing said train of signals to said criteria to provide a control signal upon achievment of end point; and
means responsive to said control signal for inactivating said means for exposing.

4. Apparatus according to claim 3, wherein said means for counting comprises adjustable timer means for selecting said interval.

* * * * *